United States Patent [19]
Fleming

[11] Patent Number: 5,241,569
[45] Date of Patent: Aug. 31, 1993

[54] IMAGING RADIONUCLIDE ANALYSIS APPARATUS AND METHOD

[75] Inventor: Ronald H. Fleming, Redwood City, Calif.

[73] Assignee: Charles Evans & Associates, Redwood City, Calif.

[21] Appl. No.: 592,355

[22] Filed: Oct. 2, 1990

[51] Int. Cl.$^5$ .............................................. G21G 1/00
[52] U.S. Cl. .................................................. 376/159
[58] Field of Search ................ 376/159, 158, 190, 194, 376/153

[56] References Cited
U.S. PATENT DOCUMENTS
3,997,787 12/1976 Fearon et al. .................. 376/159

Primary Examiner—Donald P. Walsh
Assistant Examiner—Frederick A. Voss
Attorney, Agent, or Firm—Limbach & Limbach; George C. Limbach

[57] ABSTRACT

Neutron activation analysis method and apparatus are disclosed wherein a sample in a vacuum chamber is irradiated with neutrons, the time when and energy of emitted gamma rays from a sample are detected, and delayed Beta-electrons emitted from the sample are detected and the positions of emission are imaged. Time coincidence between detected gamma rays and delayed Beta-electrons is determined and the location of elements on the sample is established from the detected coincidence and the image of the location on the sample where the delayed Beta-electrons were emitted.

5 Claims, 4 Drawing Sheets

IMAGING RADIONUCLIDE ANALYSIS APPARATUS AND METHOD

The present invention relates in general to imaging radionuclide analysis apparatus and method and more particularly to imaging neutron activation analysis apparatus and method.

BACKGROUND OF THE INVENTION

Normal neutron activation analysis measures the average concentration of one or more analytes in a single analysis volume. Neutron activation analysis is an extremely powerful method for measuring major, minor, and trace element concentrations in a wide variety of samples. Analyte elements absorb a neutron to form a radionuclide which usually decays by emitting a $\beta$-particle and a $\gamma$-ray. The $\gamma$-ray energies are characteristic of the analyte element and they are normally measured with a germanium detector. Modern germanium crystal $\gamma$-ray detectors have excellent energy resolution which provides for simultaneous in situ determination of many elements. This procedure, performed without chemical separations, is called instrumental neutron activation analysis (INAA). Although the INAA takes place on elements located in situ within unaltered samples, information on the three-dimensional locations of the elements is never acquired.

Beta-electrons provide a method for gathering lateral position information for individual radionuclide decompositions in thin samples or particles. Neutron activated nuclides usually decompose by $\beta$-decay, effectively producing a nucleus in which a neutron has been converted to a proton. The nucleus emits a neutrino, and usually a $\gamma$-ray in addition to the $\beta$-electron. The emitted electrons have substantial energies which are largely expended in the production of secondary electrons. Secondary electrons with energies of a few electron volts can be imaged if they pass out of the sample.

BRIEF SUMMARY OF THE INVENTION

Broadly stated, the present invention, to be described in greater detail below is directed to radionuclide imaging method and apparatus wherein the time when and the energy of $\gamma$-rays emitted from the sample are detected and the presence of certain elements in the sample established from the detected ray energies. Secondary electrons emitted from the sample are detected and imaged showing the location on the sample from which the secondary electrons were emitted. Coincidence between detection of $\gamma$-rays and secondary electrons is determined to establish the location of certain elements on the sample.

In accordance with a principle aspect of the present invention, the location of the certain elements on the sample is established by producing a distribution image of the certain elements of the sample from the determined coincidence of the detected rays and the detected secondary electrons and the established ray energies and the image of the location on the sample from which the secondary electrons are emitted.

Thus, when $\gamma$-rays and $\beta$-particle induced secondary electrons are detected in coincidence, the $\gamma$-ray energy answers the question of "what" and the secondary electron position answers the question "where" for individual radionuclide disintegrations.

In accordance with another aspect of the present invention, the secondary electrons are detected and imaged using an image intensifier and a resistive anode encoder.

The features and advantages of the present invention will be appreciated by a perusal of the following specification taken in conjunction with the accompanying drawings wherein similar characters of reference refer to similar elements in each of the several views.

DESCRIPTION OF THE PREFERRED EMBODIMENT

Figure 1:
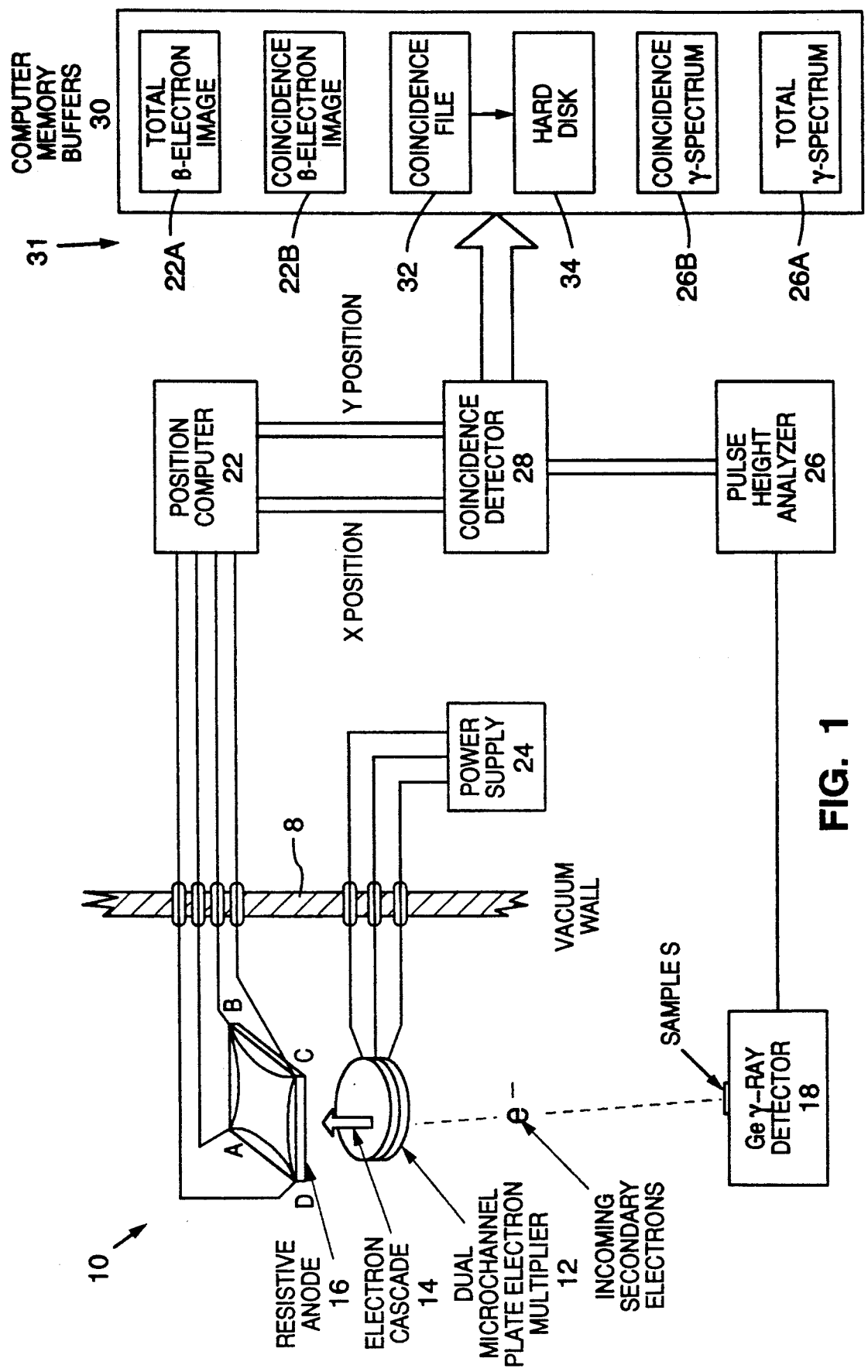
FIG. 1 is a schematic view, partially in broken away elevational sectional form and partially in block diagram form.

FIG. 1 illustrates a schematic preferred embodiment of the present invention in which the sample is positioned behind a vacuum wall 8 surrounding the charged particle optics 10 for electron extraction and imaging of secondary electrons arising when energetic $\beta$-particles pass out of the sample. The charged particle optics include a dual microchannel plate electron multiplier 12 from which the electron cascade 14 passes to the resistive anode encoder and detector 16 from which the X,Y position of the secondary electrons emitted from the sample is determined. The imaging process depends on accelerating the secondary electrons in an electric field, focusing them at a crossover point, and projecting the image onto the image intensifier 12 and detector 16. A germanium $\gamma$-ray detector 18 is positioned below the sample S.

The resistive anode encoder 16 is connected through the vacuum wall 8 to a position computer 22 and the dual microchannel plate electron multiplier 12 is connected through the vacuum wall 8 to a power supply 24. The $\gamma$-ray detector 18 is connected to a pulse height and computer based multi-channel analyzer 26, and both the analyzer 26 and position computer 22 are connected to a coincidence detector 28 for determining which nuclide disintegrations give both position and energy information.

The data from the position computer 22 and the analyzer 26 are connected to data storage sections 22A and 26A of computer memory buffers 30 of a computer 31 (not shown in detail). The coincidence detector 26 is also connected to the computer memory buffers whereby the computer system produces a coincidence $\beta$-electron image buffer 22B and coincidence $\gamma$-spectrum buffer 26B for providing the combined information to a coincidence file 32 which is stored on a hard disk 34. A data logger is provided to associate the energy and position data with a time stamp in the computer records, and computer software is provided to control and monitor the detection and to organize the data into elemental images and local area $\gamma$-ray spectra.

Figure 2:
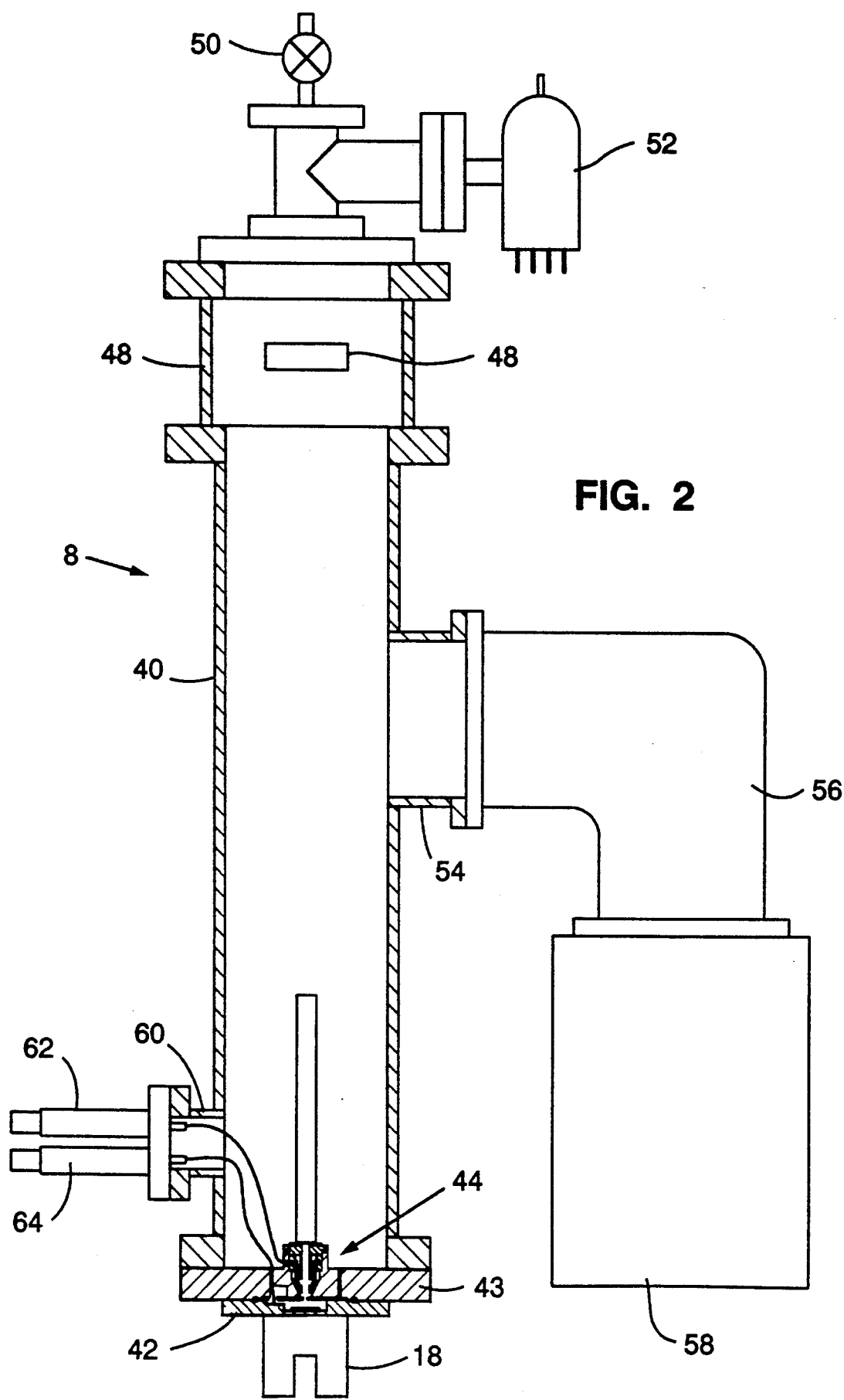
FIG. 2 is a schematic elevational sectional view of the charged particle optics for electron extraction and imaging of secondary electrons arising where energetic $\beta$-particles pass out of the sample.
Figure 3:
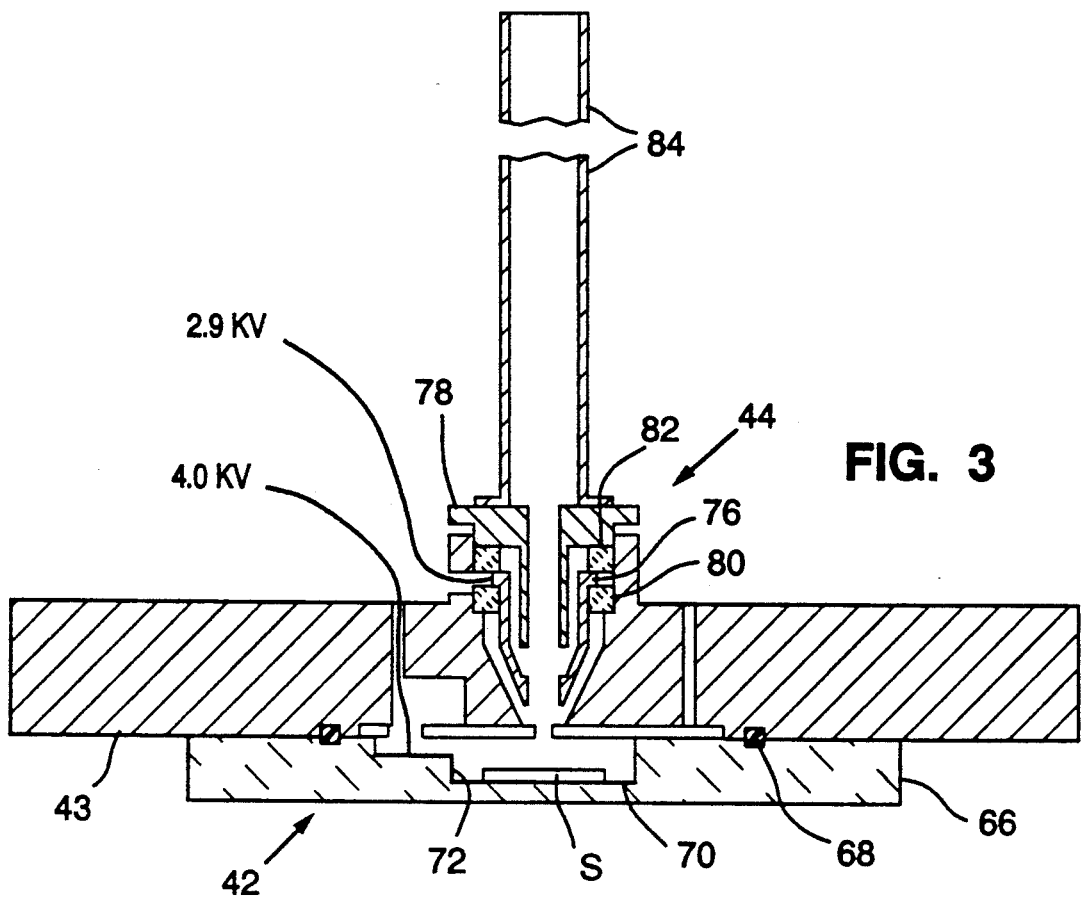
FIG. 3 is an enlarged sectional view of the charged particle optics for electron extraction shown in FIG. 2.

Referring now to FIGS. 2 and 3 there are shown the structures for the charged particle optics and secondary electron extraction and imaging optics 10 with its associated vacuum wall 8 and the germanium detector 18.

The main vacuum chamber 8 consists of a stainless steel tube 40 with the sample holder 42 mounted on a vacuum flange 43. The extraction optics 44 are supported at one end of the tube 40 and the combination dual microchannel plate electron multiplier array and resistive anode encoder detector 46 mounted in a vacuum housing 48 on the other end. The detector housing 48 has a port connecting to a bleed valve 50 for venting the system and an ion gauge for monitoring the vacuum. A tee 54 and an elbow 56 connect a turbomolecular pump 58 to the main vacuum chamber tube 40. The vacuum system which typically operates at about $4 \times 10^{-7}$ torr includes a second tee 60 having high voltage feed through 62 and 64 for the sample and focusing electrode.

The sample holder 42 consists of an insulating sample support and vacuum sealing plate 66 mounted on the vacuum flange 43 with a sealing o-ring 68. The plate 66 includes a well 70 to provide a distance of approximately 3.7 mm from the sample to the extraction lens 44. The bottom of well 70 is covered with a disk 72 such as of stainless steel to which is applied a suitable high voltage via the feedthrough 64. A sample stage, not shown, moveable in all three directions can impart desired movement between the sample and the extraction optics.

The extraction optics include an extraction lens opening 74 behind which are successively mounted a focus electrode 76 and a second electrode 78 spaced apart by insulators 80 and 82. The second electrode 78 is connected to a field free flight path tube 84.

Operation of the focusing electrode 76 in an accelerating mode confers lower chromatic aberration on the system. However, higher voltages eventually lead to arcing among components in the vacuum system. In the accelerating mode the focusing electrode 76 requires about 2.5 times the acceleration voltage. In an operative prototype embodiment of the invention, the focusing lens 76 was operated in deceleration mode at about minus 2.85 KV with the sample at minus 4.0 KV and the field free region of tube 85 at ground potential.

In the detector 46, the two plates of the dual microchannel plate electron multiplier arrays can have gains of approximately 1000 each, and when the electron cascade from the electron multiplier strikes the resistive anode encoder, the relative currents flowing from the four corner electrodes of the encoder can provide the position of the electron cascade and thus the position of the original electrons emitted from the sample.

The calculated position is based on the centroid of the electron cascade. The cascade current is variable and the resistive anode encoder electronics have both lower and upper thresholds for the electron multiplier cascade current. Several electrons arriving simultaneously (within about 100 ns.) at the detector surface produce a larger cascade roughly in proportion to the number of impinging secondary electrons. However, a central position is calculated. The position is the average position (centroid) of the impinging secondary electrons weighted according to the magnitude of their individual multiplier cascades. Since most nuclide decompositions produce more than one secondary electron, the resistive anode encoder lower threshold can be set relatively high to eliminate stray electrons, cosmic rays and other background signals.

Many factors will contribute to the lateral resolution of secondary electron images.

Resolution of the detector. The analog electronic circuits used for the position calculations can provide resolution of about one part in 400. However, digitization reduces this to one part in 256. Thus, at a magnification of 30, the smallest resolvable image feature is about 6 $\mu$m (two pixels). Smaller features can still generate measurable signals, but without information regarding feature size.

Direction of $\beta$-emission. A $\beta$-electron travelling with a velocity component parallel to the sample surface would likely produce secondary electrons laterally displaced from the nuclide disintegration. The worst case would be a $\beta$-electron travelling exactly parallel to the sample surface. Secondary electrons (relatively few) that eventually work their way to the surface have a centroid displaced from the original disintegration by half of the $\beta$-particle stopping distance. Thin samples minimize this effect. Relatively high values of the RAE lower discriminator level also help reduce the effect.

Energy spread of secondary electrons (chromatic aberration). Those $\beta$-particles passing out of the sample with large energies usually strike an instrument surface and are stopped before reaching the detector. However, off-axis components of secondary electron energy lead to loss of image resolution. The propensity to form several secondary electrons at the sample surface also tends to minimize chromatic aberration because the detector provides a centroid of the positions of the several secondary electrons. Relatively high detector lower discriminator levels favor detection of those events producing multiple secondary electrons.

Counting statistics. In high contrast images, features often emerge when only a few thousand counts are spread over relatively few pixels. However, a low contrast image requires a larger number of counts spread over many pixels. For example, if two regions within an image vary by 10% in signal intensity for a specified $\gamma$-ray energy, signal-to-noise ratios of 10 are required to distinguish the differences. This necessitates about 100 recorded disintegrations for each pixel. If the low contrast features extend over the entire image (about 50,000 pixels), a total of about $5 \times 10^6$ disintegrations must be recorded for each specified $\gamma$-ray energy. This could take a long time.

Several types of $\gamma$-ray detectors can be used. However, the best available $\gamma$-ray detectors consist of high purity n-type germanium. The outer contact is made by ion implantation of lithium and the inner contact by way of diffused lithium. An EG&G-Ortec model 8011-10185-5 GE (Li) detector (59 cm$^3$ germanium volume), a Nuclear Data Model 475 amplifier, and a Nuclear Data model 582 analog-to-digital converter can be used for the detector 18 and analyzer 26. The model 581 analog-to-digital converter is designed for high resolution processing of the amplitude modulated signals typical of solid state radiation detectors. It provides 8 to 14-bit digitizations at a rate of $1.6 \times 10^5 s^{-1}$. The conversion time is fixed at 5 $\mu$s, regardless of the input amplitude or the conversion accuracy. The constant conversion time allows the data ready signal from the analog-to-digital converter to be used in the coincidence circuitry.

The electronic coincidence detection circuit 28 accepts x- and y- position data from the position detectors analog-to-digital converters in position computer 22, an γ-ray energy data from the germanium detectors analog-to-digital converter. In the operative embodiment the output of the coincidence detector 28 is 32 bits of data. Since 16 bits of position information and 13 bits (8192 channels) of energy information are used, a 32 bit long word can accommodate three indicator bits. One indicator bit each is dedicated to indicating valid position, energy, and coincidence data.

The position information arrives at the coincidence detector 28 first because the position detector electronics have a shorter dead time than the γ-detector. The position detector dead time is constant (3.0 $\mu$s) and is fixed on the position computer by an electronic timer (a one-shot). When position data arrive at the coincidence detector 28, the valid position bit is set and a delay timer is started. The end of the delay period starts the coincidence window timer. If the γ-ray energy data arrives from the analog-to-digital converter in the coincident window, then the valid coincident bit is set. If the γ-ray energy data arrive before or during the delay period, the valid energy bit is set. It is possible to have valid position and energy data in the same long word without having a valid coincidence. When the timers have timed out, the three indicator bits are added to the data lines, a strobe (handshake) pulse is sent to the computer parallel interface, and the energy and position data are passed through to the parallel interface. The delay and window times are adjustable and are set at 7.6 and 1.8 82 s, respectively in the operative embodiment. The total time between the nuclide decomposition and clocking the data into the computer is typically 11.5 $\mu$s (7.6+3.0+1.8/2). Since the γ-ray analog-to-digital converter has a fixed conversion time of 5 $\mu$s, the germanium detector, preamplifier and amplifier combination must require about 6.5 $\mu$s. This setting is variable over a range of about 1 $\mu$s. Different energies require slightly different setting times. This can result in distortion of the γ-ray spectrum if the coincidence delay and internal times are incorrectly set.

The β-particle position and the γ-ray energy data come into the computer 31 via a parallel interface. In an operative embodiment, the computer 31 is a CompuAdd 386 SX with an 80387 SX arithmetic co-processor 2 Mbyte of random access memory, a 40 Mbyte hard disk drive, two floppy disk drives, a streaming tape mass storage unit, and a high resolution graphics interface.

As 32-bit data words arrive at the computer parallel interface, an interrupt service routine (ISR) places the new data into a buffer. When the computer is not busy with the ISR, it can process the data out of the buffer in the first in first out order. If the computer goes to other tasks such as keyboard service routines or disk input-output, the ISR continues to store new data into the buffer. Since the buffer has 64 Kbytes of computer memory, the computer can be away at those other tasks for considerable time without missing any input data.

The data is processed out of the input buffer 30 into five separate areas of computer memory. For the total spectrum buffer 26A the energy channel specified in each of the 32-bit input data word is incremented if that data word has a valid energy or coincidence bit. Energy channels use four bytes each. Thus, the total spectrum requires a data buffer of 32 Kbytes. This is the standard multi-channel analyzer function in which the resulting spectrum is independent of any coincidence condition.

For the coincidence spectrum buffer 26B, the energy channel specified in each 32-bit input word is incremented if that data word has a valid coincidence bit. This spectrum also requires 32 Kbytes of computer memory. It is mainly useful for monitoring the operation of the coincidence detector 28 and computer interface.

For the total electron image buffer 22A the image position specified in each 32-bit input data word is incremented if that data word has a valid position or coincidence bit. Images require a 128 Kbyte data buffer in computer memory. Like the total spectrum buffer 26A, the total image buffer 22A is independent of the coincidence condition.

For coincidence image buffer 22B the energy channel specified in each 32-bit input data word is incremented if the data word has a valid coincidence bit. Before data acquisition, the operator is polled for the upper and lower boundaries of an energy window. Only those image positions associated with energies in the energy window are incremented. If the selected energy window contains a single peak of the γ-spectrum, then the coincidence image constitutes a position map of the isotope responsible for the γ-rays. During data acquisition, both the total image buffer 22A and the coincidence image buffer 22B are available in real time for monitoring the experiment.

For the coincidence file buffer 32, whenever the valid coincidence bit is set, the energy and position data and a 16-bit time stamp are associated and logged into the computer memory buffer 32. This memory buffer occupies 256 Kbyte. When it is full, the contents are dumped to a hard disk file 34. The ISR continues to place new data into the input buffer, even during 15 disk operations. Thus, no data are lost under normal operation.

As soon as data acquisition begins, the computer displays the total γ-ray spectrum in real time. During data acquisition, the operator can examine any region of the total or coincidence γ-ray spectrum with a linear or logarithmic display including any amount of y-axis offset. All of the spectral displays are continuously updated as new data are acquired. If the operator chooses image display, the system furnishes continuously updated total and coincidence images with either linear or logarithmic scale.

All of these display features are available after the data acquisition is complete. In addition, there are options for labelling the displays and entering identification comments. The operator can store any or all of the images and spectra to a computer hard disk and can reaccess any stored spectra. The coincidence files are automatically stored if the operator selects this feature at the start of data acquisition. There are utilities for integration of spectral peaks and for printing spectra on a color printer.

Finally, element maps and local area γ-ray spectra can be prepared from stored coincidence file data. Thus, the operator need not specify or even know before beginning the analysis what coincidence images or spectra will be needed. Positions from those data records having energies within an operator selected window can be organized into an element map. Similarly, energies from those data records having positions within a operator selected area window can be organized into a local area spectrum. These two possibilities are implemented as menu choices in the imaging neutron activation analysis software. These two options bring the total number of available menu operations to 38.

Figure 4:
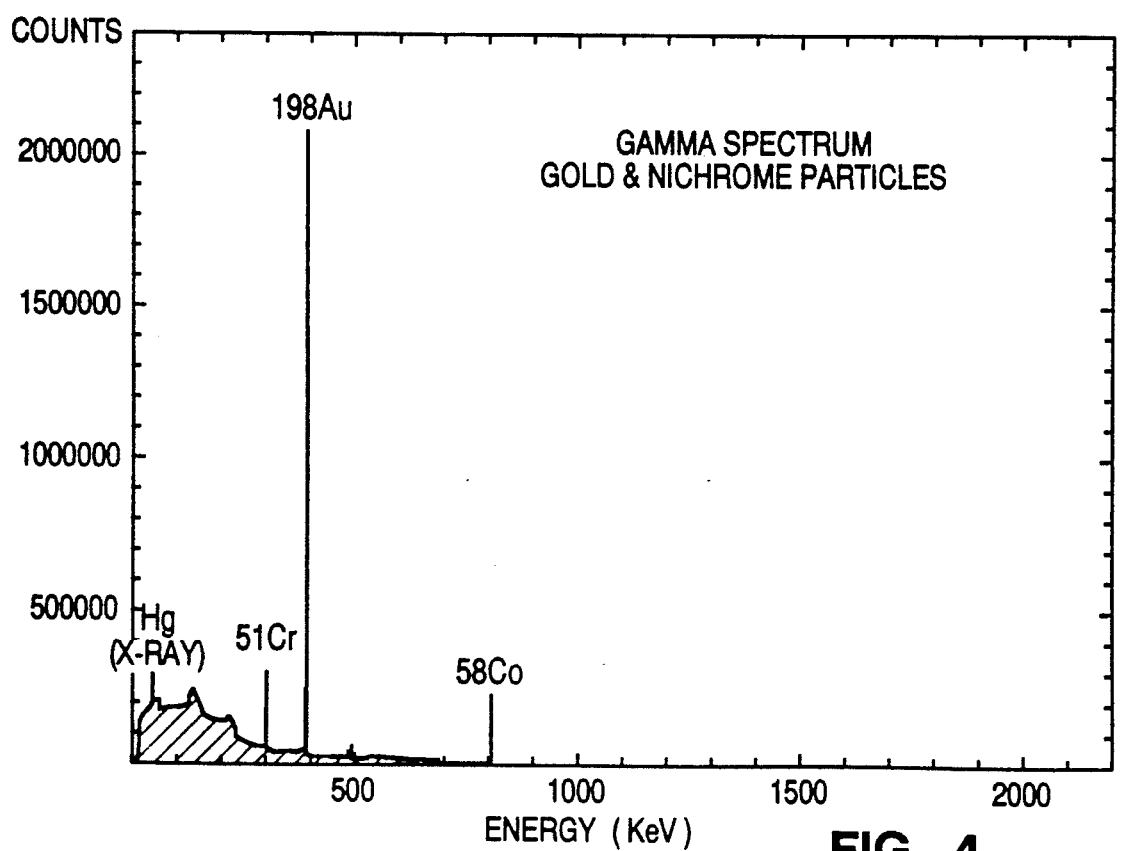
FIG. 4 is a graph of electron counts plotted against energy level of detected $\gamma$-rays in an operative example of use of the present invention.
Figure 5A:
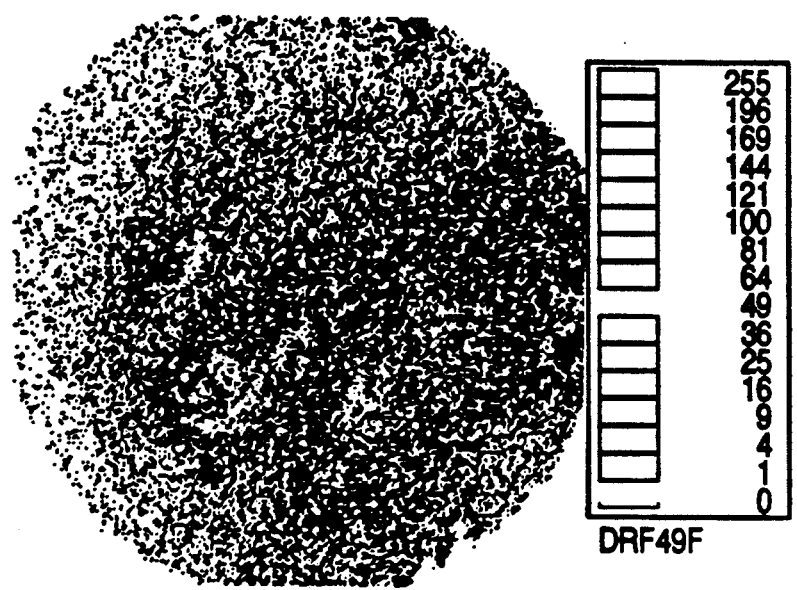
FIGS. 5A and 5B illustrate the distributions of gold and nickel, respectively, on a portion of a particle sample.
Figure 5B:
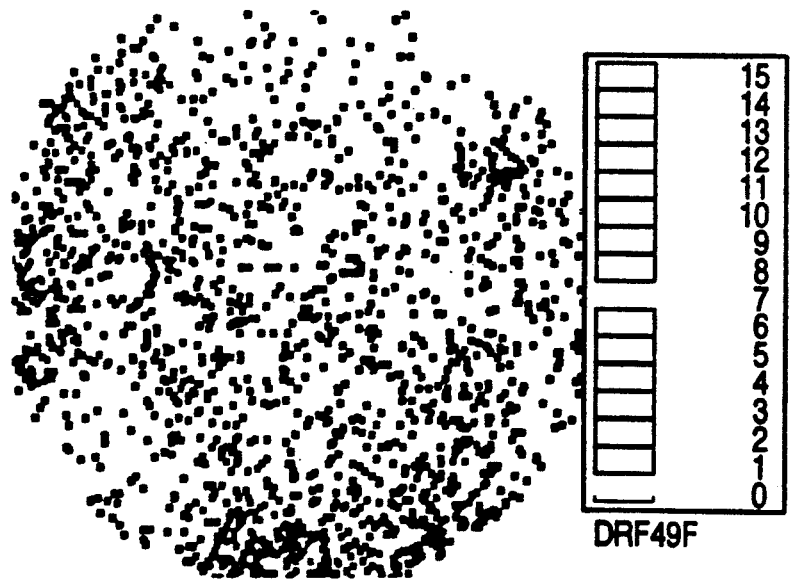

An example of operation of the present invention is illustrated in FIGS. 4, 5A and 5B. The sample from which these figures were derived consisted of particles of irradiated gold and nichrome dispersed on a piece of silicon wafer. The γ-ray spectrum of the particle mixture is shown in FIG. 4. FIG. 4 shows the γ-signals arising from radioactive chromium ($^{51}$Cr) gold ($^{198}$Au) and nickel ($^{58}$Co). Neutron irradiation of $^{58}$Ni produces $^{58}$Co, and when $^{198}$Au emits an electron, it becomes $^{198}$Hg. The distributions of gold and nickel on a portion of the particle sample are shown in FIGS. 5A and 5B, respectively. The area covered by the images is about 0.9 mm.

There are various potential applications for the imaging neutron activation analysis of the present invention. The distribution of trace elements among mineral phases is a prime concern of geochemists. Better analysis techniques spur development of sophisticated models for partitioning of trace elements between minerals, magmas, and hydrothermal solutions. The models infer the evolution of igneous rocks and associated ore deposits from trace element signatures, especially rare earth signatures. Many interplanetary dust particles could be simultaneously counted with a single imaging detector using the present invention. Additionally, high purity ceramic materials find increasing use in many modern applications, perhaps most significantly in the electronics industry. For such materials imaging neutron activation analysis can be microanalytical, sensitive, accurate, unsusceptible to sample charging and independent of sample matrix.

Materials containing radioactive nuclides for reasons other than neutron activation analysis will also benefit from the imaging γ-ray detector of this invention. Natural and nuclear industry induced radionuclides are often heterogeneously distributed within a sample. For example, imaging secondary ion mass spectrometry suggests the presence of transuranic elements and the possibility of radioactive rare earth elements concentrated in various tissues in marine organisms living near French nuclear power facilities. Imaging with the present invention can provide much better sensitivity for the transuranic elements and radioactive fission fragments, free from the extensive interferences found in secondary ion mass spectrometry analysis of complex samples.

Charged particle activation often complements neutron activation insensitivity and provides a unique set of experimental advantages. High energy ions of $^1$H, $^2$H, $^3$He, $^4$He, as well as heavier species can induce nuclear processes. For example, 5.5 MeV protons activate iron by the $^{56}$Fe (pn) $^{56}$Co reaction. The $^{56}$Co undergoes β+ (positron) decay with a half-life of 74 days and a characteristic 747 KeV γ-ray. Ion beam activation occurs in the top several microns of a sample surface which is convenient because the secondary electrons can escape from about the implantation depth of the activating ion beam.

The terms and expressions which have been employed here are used as terms of description and not a limitation, and there is no intention, in the use of such terms and expressions, of excluding equivalence of the features shown and described, or portions thereof, it being recognized that various modifications are possible within the scope of the invention claimed.

I claim:

1. Imaging neutron activation analysis apparatus comprising:
   a vacuum chamber,
   means for positioning a sample in said vacuum chamber,
   means for irradiating the sample with neutrons,
   means for detecting the time when and the energy of gamma rays emitted from the sample and for establishing from the detected gamma ray energies the presence of certain elements in the sample,
   means for detecting when delayed Beta-electrons are emitted from the sample and for imaging the location on the sample from which such delayed Beta-electrons are emitted,
   means for determining time coincidence between detection of gamma rays by said gamma ray detecting means and detection of electrons by said delayed Beta-electron detecting means and
   means for establishing the location of certain elements on the sample from determined coincidence of detected gamma rays and detected delayed Beta-electrons and the established gamma ray energies and the image of the location on the sample from which such delayed Beta-electrons are emitted.

2. The apparatus of claim 1 wherein said means for establishing the location of certain elements includes means for producing a distribution image of the certain elements of the sample from determined coincidence of detected gamma rays and detected delayed Beta-electrons and the established gamma ray energies and the image of the location on the sample from which such delayed Beta-electrons are emitted.

3. The apparatus of claim 1 wherein said means for detecting and imaging delayed Beta-electrons includes image intensifying means and resistive anode encoder means.

4. An imaging neutron activation analysis method for analyzing certain elements of a sample comprising:
   irradiating a sample with neutrons,
   detecting the time when and the energy of gamma rays emitted from the irradiated sample,
   establishing from the detected gamma ray energies the presence of certain elements in the sample,
   detecting when delayed Beta-electrons are emitted from the sample and imaging the location on the sample from which such delayed Beta-electrons are emitted,
   determining time coincidence between detection of gamma rays by said gamma ray detecting step and said delayed Beta-electron detecting step and
   establishing the location of certain elements on the sample from determined coincidence of detected gamma rays and detected delayed Beta-electrons and the established gamma ray energies and the image of the location on the sample from which such delayed Beta-electrons are emitted.

5. The method of claim 4 wherein said step of establishing the location of certain elements on the sample includes producing a distribution image of the certain elements of the sample from determined coincidence of detected gamma rays and detected delayed Beta-electrons and the established gamma ray energies and the image of the location on the sample from which such delayed Beta-electrons are emitted.

* * * * *